US009322767B2

(12) United States Patent
Ehrenkranz

(10) Patent No.: US 9,322,767 B2
(45) Date of Patent: Apr. 26, 2016

(54) DEVICE FOR PERFORMING A BLOOD, CELL, AND/OR PATHOGEN COUNT AND METHODS FOR USE THEREOF

(71) Applicant: Joel R. L. Ehrenkranz, Salt Lake City, UT (US)

(72) Inventor: Joel R. L. Ehrenkranz, Salt Lake City, UT (US)

(73) Assignee: i-calQ, LLC, Salt Lake City, UT (US)

( * ) Notice: Subject to any disclaimer, the term of this patent is extended or adjusted under 35 U.S.C. 154(b) by 227 days.

(21) Appl. No.: 13/862,188

(22) Filed: Apr. 12, 2013

(65) Prior Publication Data

US 2013/0273524 A1 Oct. 17, 2013

Related U.S. Application Data

(60) Provisional application No. 61/684,648, filed on Aug. 17, 2012, provisional application No. 61/625,396, filed on Apr. 17, 2012.

(51) Int. Cl.
*G01N 15/06* (2006.01)
*G01N 33/00* (2006.01)
*G01N 33/48* (2006.01)
*G01N 21/17* (2006.01)
*G01N 21/84* (2006.01)
*B01L 3/00* (2006.01)
*G01N 35/00* (2006.01)
*G01N 15/10* (2006.01)
*G01N 15/14* (2006.01)

(52) U.S. Cl.
CPC ............ *G01N 21/17* (2013.01); *G01N 15/1463* (2013.01); *G01N 15/1484* (2013.01); *G01N 21/8483* (2013.01); *B01L 3/5027* (2013.01); *G01N 2015/1006* (2013.01); *G01N 2015/1486* (2013.01); *G01N 2035/00881* (2013.01); *G01N 2035/00891* (2013.01)

(58) Field of Classification Search
CPC ........ G01N 15/06; G01N 33/00; G01N 33/48
USPC .......... 422/50, 68.1, 502, 503, 509, 553, 554, 422/62, 63; 436/43, 174, 180
See application file for complete search history.

(56) References Cited

U.S. PATENT DOCUMENTS

| 5,051,238 | A | * | 9/1991 | Umetsu et al. ................... 422/64 |
| 5,320,966 | A | * | 6/1994 | Mitsumaki et al. ............. 436/47 |
| 6,784,981 | B1 | | 8/2004 | Roche et al. |
| 7,485,464 | B2 | | 2/2009 | Platano et al. |

(Continued)

OTHER PUBLICATIONS

International Search Report in PCT/US13/36459 mailed Aug. 2, 2013.

*Primary Examiner* — Brian J Sines
(74) *Attorney, Agent, or Firm* — Workman Nydegger; Perry Brown

(57) ABSTRACT

Devices and methods for performing a point of care blood, cell, and/or pathogen count or a similar blood test. Disclosed herein are systems that can be used to provide rapid, accurate, affordable laboratory-quality testing at the point of care. The systems described herein are capable of imaging and counting individual cells in a prepared cell sample (e.g., a peripheral blood smear or a blood sample prepared in a microfluidic device) or another prepared cell-containing sample without the need for a microscope or other expensive and cumbersome optics. The systems described herein are designed to eliminate or replace expensive, centralized clinical testing equipment and technical personnel. Such systems may include automated data reporting and decision support.

20 Claims, 11 Drawing Sheets

(56) References Cited

U.S. PATENT DOCUMENTS

| | | | |
|---|---|---|---|
| 8,717,556 B2* | 5/2014 | Salsman | 356/246 |
| 2001/0048899 A1* | 12/2001 | Marouiss et al. | 422/100 |
| 2005/0051723 A1 | 3/2005 | Neagle et al. | |
| 2012/0045786 A1 | 2/2012 | Stith | |
| 2012/0088230 A1 | 4/2012 | Givens et al. | |

* cited by examiner

DEVICE FOR PERFORMING A BLOOD, CELL, AND/OR PATHOGEN COUNT AND METHODS FOR USE THEREOF

RELATED APPLICATIONS

This application claims the benefit of and priority to U.S. Prov. Pat. App. Ser. No. 61/625,396 filed 17 Apr. 2012 and U.S. Prov. Pat. App. Ser. No. 61/684,648 filed 17 Aug. 2012, the entireties of which are incorporated herein by reference.

BACKGROUND

Sampling and testing of biological samples and body fluids (e.g., saliva, blood, urine, fecal matter, foods, plants, fish, minerals, animals, etc.) is common for both testing and monitoring humans, fish, animals, and plants for any number of biochemical or physiological conditions and, of course, for determining the general state of health of an organism. For example, sampling and testing of human body fluids is often performed for point-of-care testing ("POCT"). POCT is defined as medical testing at or near the site of patient care. The driving notion behind POCT is to bring the test conveniently and immediately to the patient. This increases the likelihood that the patient, physician, and care team will receive the results more quickly. This allows for immediate clinical management decisions to be made. POCT examples include, but are not limited to, blood glucose testing, metabolic testing (e.g., thyroid stimulating hormone), blood gas and electrolytes analysis, rapid coagulation testing, rapid cardiac markers diagnostics, drugs of abuse screening, urine testing, pregnancy testing, fecal occult blood analysis, food pathogen screening, hemoglobin diagnostics, infectious disease testing, cholesterol screening, cancer testing (e.g. PSA), hormone testing (hCG, LH, FSH), cardiac (troponin), pulmonary, gastroenterology (e.g., *H. pylori* antibodies), urology, nephrology dermatology, neurology, pediatrics, surgical, and public health (Ebola, cholera, HIV, malaria), and combinations thereof.

One testing method that is often employed for POCT and more conventional testing involves the use of lateral-flow chromatographic immunoassay cassettes. Lateral-flow chromatographic immunoassay cassettes can be used to easily and quickly obtain a variety of qualitative results relating to a number of biochemical and physiological conditions and disease states of an individual. These kinds of tests require the end user to simply add a sample to the cassette and then observe the result a few minutes later. Since such rapid and easy-to-use tests are user friendly, they are very popular in both the professional and consumer markets nowadays. Such tests are also very popular in areas where access to trained health care professionals is limited or where access to proper medical facilities is limited (e.g., poor areas, developing countries, war zones, etc.).

At present, there exists no means for performing more complex blood tests (e.g., a CBC, $CD4^+$ T lymphocyte count, bacterial cell count, detection of circulating parasites such as intra-erythrocyte malaria pathogens and filaria, and the like) at point-of-care or in a resource-limited setting. For example, there are well-known automated and manual methods for performing a CBC, but either class of methods requires complex and expensive instrumentation and highly skilled operators. Likewise, samples (e.g., blood) must be collected, prepared and sent off for testing, which is time-consuming. Consequently, there exists a need in the art for simple, robust technologies that can perform a blood test at the point-of-care or in a resource-limited setting to allow medical practitioners to diagnose a variety of conditions without being tied to a medical facility or a testing laboratory.

BRIEF SUMMARY

Devices and methods for performing point of care blood, cell, and/or pathogen count or a similar test. Disclosed herein are systems that can be used to provide rapid, accurate, affordable laboratory-quality blood testing at the point of care. The systems described herein are capable of imaging and counting individual cells in a prepared cell sample (e.g., a peripheral blood smear or in a fluid channel of a microfluidic device) or another prepared cell-containing sample without the need for a microscope or other expensive and cumbersome optics. The devices described herein are designed to eliminate or replace expensive, centralized clinical testing equipment and technical personnel. Such systems may include automated data reporting and decision support.

In one embodiment, a system for performing an automated cell count (e.g., an automated blood, cell, and/or pathogen count) is disclosed. The testing system includes (1) a testing device having data collection and data analysis capabilities and the ability to interface with a means for performing a blood, cell, and/or pathogen count and (2) a testing apparatus communicatively coupled to the testing device. The testing apparatus includes an image sensor and a port configured such that the means for performing the blood, cell, and/or pathogen count can be inserted into the testing apparatus and positioned in proximity to an image sensor configured to collect an image of sufficient resolution for discerning individual cells in the image taken of the means for performing the blood, cell, and/or pathogen count. The image sensor is preferably positioned inside a housing of the testing apparatus in a light controlled environment such that the image sensor is kept in substantially total darkness until the sensor is selectively illuminated for taking an image of a peripheral blood smear.

The system further includes (3) a light source capable of transmitting at least one wavelength of light configured to allow the image sensor to capture at least one image of the means for performing the blood, cell, and/or pathogen count, and (4) an automated peripheral blood differential counting system stored in a computer readable format and electronically coupled to the testing device, wherein the automated peripheral blood differential counting system is configured to count individual cells in at least a portion of the means for performing the blood, cell, and/or pathogen count and classify them according to cell type.

Suitable examples of means for performing a blood, cell, and/or pathogen count include, but are not limited to, a glass side or the like configured for preparing a peripheral blood smear or a microfluidic device configured for performing a cell count. In one embodiment, the microfluidic device may include a body that includes a counting chamber configured for performing a cell count and at least one fluid channel in fluid communication with the counting chamber for introducing a sample into the counting chamber, wherein the counting chamber includes a fixative for immobilizing one or more cells present in the sample in the counting chamber. In one embodiment, the microfluidic device includes means for measuring hemoglobin through spectrophotometric, chemical, or immunologic methods. Hemoglobin information, along with cell count data and image analysis parameters, can be used, for example, to calculate hematocrit and red cell characteristics.

In one embodiment, the at least one fluid channel further includes (1) a sample port and a dilution port in fluid communication with a dilution chamber, the dilution chamber being in fluid communication with the counting chamber and a fixing fluid port, (2) a stain port in fluid communication with the counting chamber and configured for introducing at least one cell contrast stain into the counting chamber, (3) at least one wash port in fluid communication with the counting chamber and configured for introducing at least one washing buffer into the counting chamber, and (4) a waste chamber in fluid communication with the counting chamber and configured for capturing waste fluid from the counting chamber.

In one embodiment, the at least one fluid channel further includes (1) a first reservoir containing a predetermined amount of a dilution buffer in fluid communication with a dilution chamber, the dilution chamber being in fluid communication with the counting chamber, (2) a second reservoir containing a predetermined amount of a stain in fluid communication with the counting chamber, and (3) at least a third reservoir containing a predetermined amount of a wash buffer in fluid communication with the counting chamber. In one embodiment, the first reservoir, the second reservoir, and the at least third reservoir include blister packs configured to be punctured for successively introducing each of the dilution buffer, the stain, and the wash buffer into the at least one fluid channel. In one embodiment, the at least one fluid channel may further include a fixative for fixing cells in the counting chamber and a means for drying the cells. For example, cells in the counting chamber can be dried by allowing water to evaporate under ambient conditions or under reduced atmospheric pressure and/or elevated temperature, flowing air through the fluid channel, including a drainage system, combinations thereof, and the like.

Suitable examples of testing devices that can be used with the testing system described herein include, but are not limited to, digital camera devices, cellular telephones, smart telephones, and tablet computers. Preferably, the testing device is a device that is capable of connecting to a cellular telephone network for receiving and uploading data.

In another embodiment, a method for performing an automated blood, cell, and/or pathogen count is disclosed. The method includes (1) providing a means for performing a blood, cell, and/or pathogen count, (2) preparing a cell sample for counting using the means, (3) providing a testing device having data collection and data analysis capabilities and the ability to interface with the means for means for performing the blood, cell, and/or pathogen count, and (4) inserting the means for means for performing the blood, cell, and/or pathogen count into a testing apparatus. The testing apparatus includes an image sensor, and a port configured such that the means for means for performing the blood, cell, and/or pathogen count can be inserted into the testing apparatus and positioned in proximity to the image sensor.

The method further includes (5) illuminating the cell sample with at least one wavelength of light configured to allow the image sensor to capture at least one image of the cell sample, and (6) querying an automated counting system stored in a computer readable format and electronically coupled to the testing device, wherein the automated counting system is configured to count individual cells in at least a portion of the cell sample and classify them according to cell type.

In one embodiment, the cell sample prepared with the means may include at least one cell-specific antibody that can make it possible to selectively image selected cells in the cell sample. Antibodies can also be used to selectively fix cells to the means. In one embodiment, selective imaging of selected cells in the cell sample is facilitated by coupling the at least one cell-specific antibody to at least one detectable label.

Suitable examples of detectable labels include, but are not limited to, colored beads, colloidal gold, colloidal silver, dyes, fluorescent dyes, quantum dots, and combinations thereof.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Introduction

Disclosed herein are testing devices and methods that can be used to provide an automated, rapid, accurate, affordable laboratory-quality cell count (e.g., an automated blood and/or cell and/or pathogen count). For example, the testing devices and methods can be used for evaluating a peripheral blood smear or a similar blood sample at the point of care without the need for a microscope or other expensive and cumbersome optics. Alternatively, the devices and methods described herein can be used for counting individual cells in a micro fluidic device without the need for a microscope or other expensive and cumbersome optics.

In one embodiment, a blood count consists of counting at least one of red blood cells, white blood cells, platelets, or other blood factors and cells in a given volume of blood, and measuring hemoglobin concentration. The blood count may also include determining one or more of the percentage of granulocytes, lymphocytes, eosinophils, basophils, and monocytes, or calculating the mean red cell volume, hemoglobin, and hematocrit.

A peripheral blood smear (sometimes also referred to as a "peripheral blood film") generally consists of a drop of venous blood that is spread out in a thin layer on one surface of a glass microscope slide or a similar surface. Typically, the peripheral blood smear is stained with a dye (e.g., Wright's stain), and examined under a microscope. In such a system, cells are typically counted manually by a technician or by an automated image analysis software computer and microscope.

Figure 1:
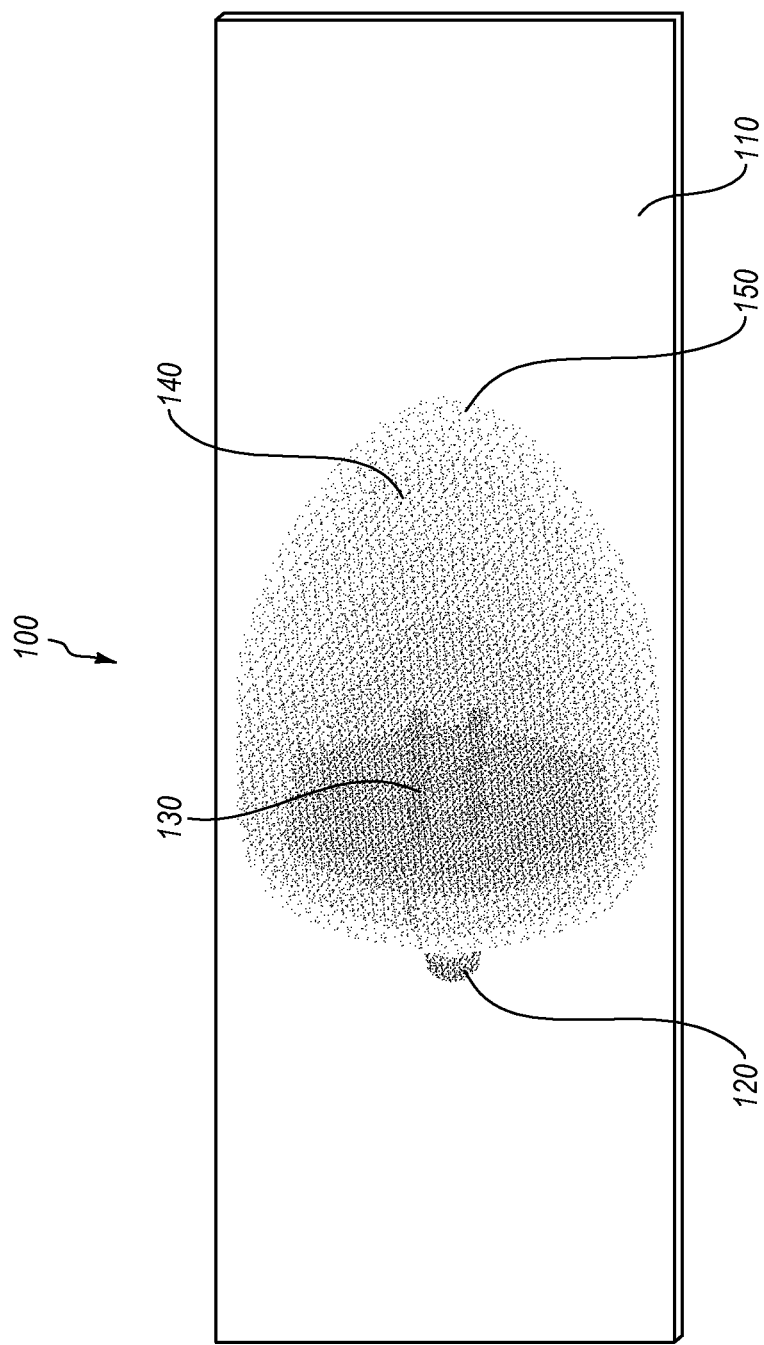
FIG. 1 illustrates a peripheral blood smear.

Referring to FIG. 1, a peripheral blood smear 100 prepared on a glass slide 110 (e.g., a glass microscope slide) is illustrated. The peripheral blood smear 100 includes a head 120, a body 130, a zone 140 that is distal to the body 130, and a tail 150. A well-made peripheral smear 100 is typically thick near the head 120 and becomes progressively thinner toward the tail 150. The blood smear in the head 120 region, which shows evidence of the area where the blood was spotted onto the slide 110, and the body 130 are typically too thick to discern individual blood cells. However, individual cells can typically be discerned and counted in zone 140 (generally referred to as the "zone of morphology") and the tail 150.

Preparing the peripheral blood smear 100 on a transparent slide 110 typically includes: (1) collecting a blood sample from a subject, (2) placing a drop of blood from the blood sample on the transparent slide (e.g., a glass microscope slide), (3) contacting the drop of blood with a spreader (e.g., a second glass microscope slide), (4) spreading with the spreader the drop of blood on the transparent slide from a first end to a second end to form a blood smear, and air drying the blood smear to yield the peripheral blood smear.

Contacting the drop of blood with a spreader and spreading with the spreader includes (a) contacting the first slide with the spreader slide distal to the blood spot, (b) drawing the spreader slide proximally at an angle of ~30° until the spreader slide contacts the blood spot (the blood will spread along the edge of the spreader slide by capillary action), and (c) pushing the spreader slide distally along the first slide while maintaining the ~30° angle.

Preparing the peripheral blood smear on a transparent slide may further include (5) fixing the peripheral blood smear in alcohol, and (6) staining the peripheral blood smear with a stain. For example, Wright's stain may be used to stain the peripheral blood smear.

Visual analysis of a peripheral smear 100 generally requires a systematic approach in order to gather all possible information. In addition, all specimens must be evaluated in the same manner, to assure that consistent information is obtained. As can be readily appreciated from the following, visual analysis of a peripheral smear 100 is a complicated and time consuming process that requires a skilled technician. The following approach is recommended for visual inspection/analysis of a peripheral blood smear:

An examination at low power (10× ocular, 10× objective) is first performed to evaluate the quality of the smear, ascertain the approximate number of white blood cells and platelets, and to detect stacking of cells, platelet clumps, and leukocyte clumps and other abnormalities visible at low magnification. A selected area for evaluation at higher magnification is also chosen. This should be an intact portion of the smear free of preparation artifacts where the red blood cells are separated by ⅓ to ½ of a cell diameter. The red blood cells should stain a pink color, while neutrophils show "crisp" features, with deep blue-purple nuclear material and lilac to pinkish to violet cytoplasmic granules.

Following low power examination of a peripheral blood smear, the 50× or 100× objective of the microscope is selected (500× or 1000× total magnification when using a 10× ocular) and the area of morphology is examined in a consistent scanning pattern (e.g., a zig-zag pattern) to avoid counting cells twice. A differential count of at least 100 white blood cells (200, 500, or 1000 is even better) is performed, and any abnormal morphology of RBCs, WBCs, and platelets observed during the differential count is recorded.

A fairly accurate estimate of the white blood cell count (cells/μL) can be obtained by counting the total number of leukocytes in ten 500× microscopic fields, dividing the total by 10, and multiplying by 3000. However, the statistical reliability of manual counts of peripheral blood smears is questionable.

In contrast to manual procedures, the devices and methods described herein provide means for imaging and counting individual cells in a peripheral blood smear without the need for a microscope or other expensive and cumbersome optical devices. The devices described herein are designed to eliminate or replace expensive, centralized clinical testing equipment and technical personnel. Such devices may include automated data reporting and decision support.

II. Systems for Performing an Automated Blood, Cell, and/or Pathogen Count

Figure 2B:
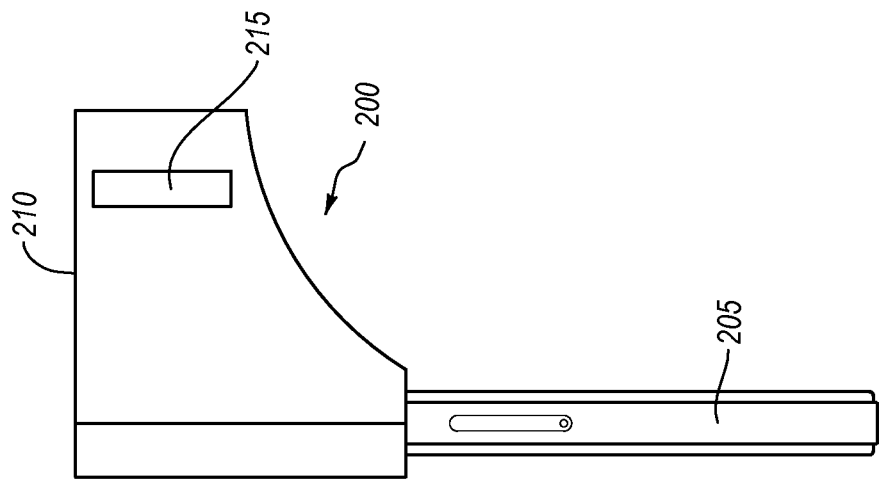
FIG. 2B illustrates a side view of the system of FIG. 2A.
Figure 2A:
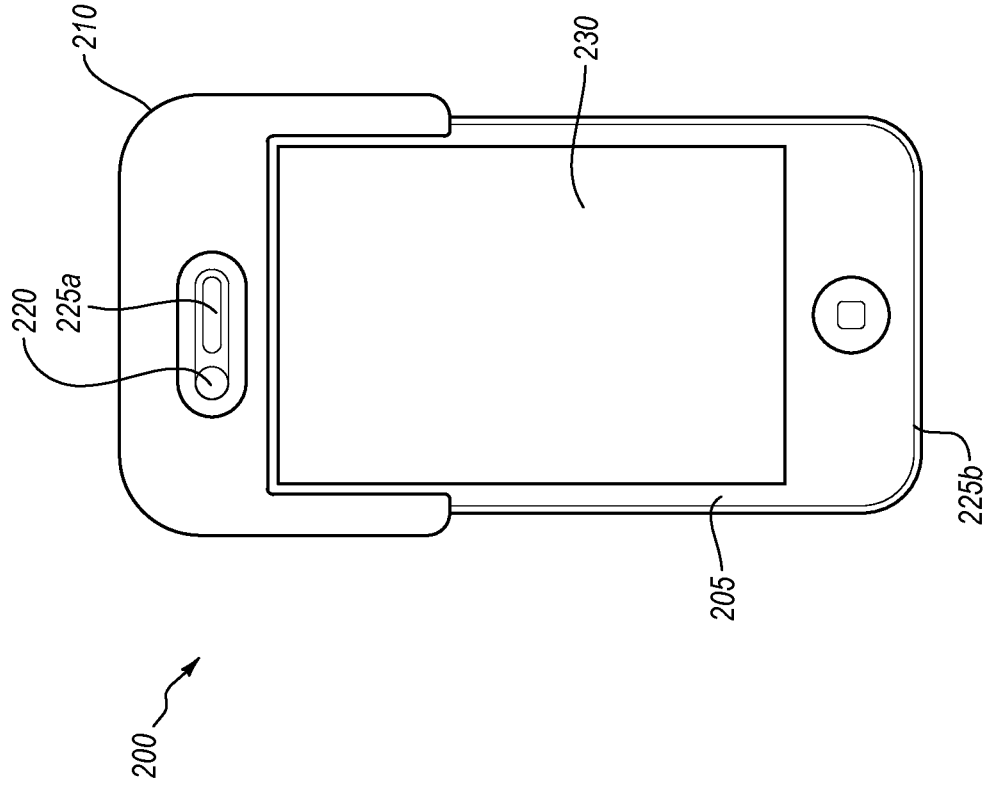
FIG. 2A illustrates a plan view of a system for performing an automated blood, cell, and/or pathogen count that includes a testing device and a testing apparatus configured to couple a peripheral blood smear to the testing device.

Referring now to FIGS. 2A and 2B, plan and side views of a system for performing an automated blood, cell, and/or pathogen count diagnostic test system 200 are illustrated. The illustrated system 200 includes a testing device 205 and a testing apparatus 210 that is attached to the testing device 205.

In the illustrated embodiment, the testing device 205 is an iPhone. However, the testing 205 device can be essentially any cell phone device, digital camera device, or a similar device that has an onboard camera/image capture function, data collection and analysis capabilities (i.e., computing functions), data and results display capabilities, and, preferably, the ability to communicate with one or more remote computer networks for data upload, querying a data analysis algorithm, querying a decision support algorithm, and the like. In the illustrated embodiment, the testing device 205 includes a front-directed camera 220, a back-directed camera (not shown) that is directed into the testing apparatus 210, a display screen 230, and audio input and output ports 225a and 225b. The front-directed camera 220 may be used to photograph a prepared blood sample (e.g., a peripheral blood smear) (see, e.g., FIG. 1) prior to analysis. In one embodiment, the photograph of the prepared blood sample may be uploaded to a computer network for visual assessment of the quality of the prepared blood sample by a trained medical technologist. The display screen 230 can be used for display of data and results. In addition, the display screen 230 may include touchscreen capabilities that can be used for input of data or commands.

The testing apparatus 210 is designed to be securely coupled to the testing device 205. For example, the testing apparatus 210 may be designed to fit a specific class or brand of testing devices. The testing apparatus 210 includes a port 215 that is designed to allow a prepared blood sample, such as the peripheral blood smear 100 illustrated in FIG. 1, to be inserted into the testing apparatus 210. Additionally, an interior portion of the testing apparatus 210 may be painted with a flat black color so as to avoid extraneous and reflected light.

In addition, the testing apparatus 210 includes a number of internal components (e.g., image sensors, i/o ports, power ports, light source(s), lens(es), light conducting media, etc.) that are designed to transform the testing device 205 into a device that can be used to collect and analyze data from a prepared blood sample and access an automated peripheral blood differential counting system is configured to count individual cells in at least a portion of the prepared blood sample and classify them according to cell type.

While the testing apparatus 210, is shown fitted to the testing device 205, one will appreciate that the testing apparatus can be configured as a separate unit that includes its own power source, light source, optics, data capture capabilities, data processing capabilities, and the like. In such an embodiment, the testing apparatus may be configured to collect assay data from prepared blood sample and transfer it to the testing device for analysis and reporting.

Figure 2C:
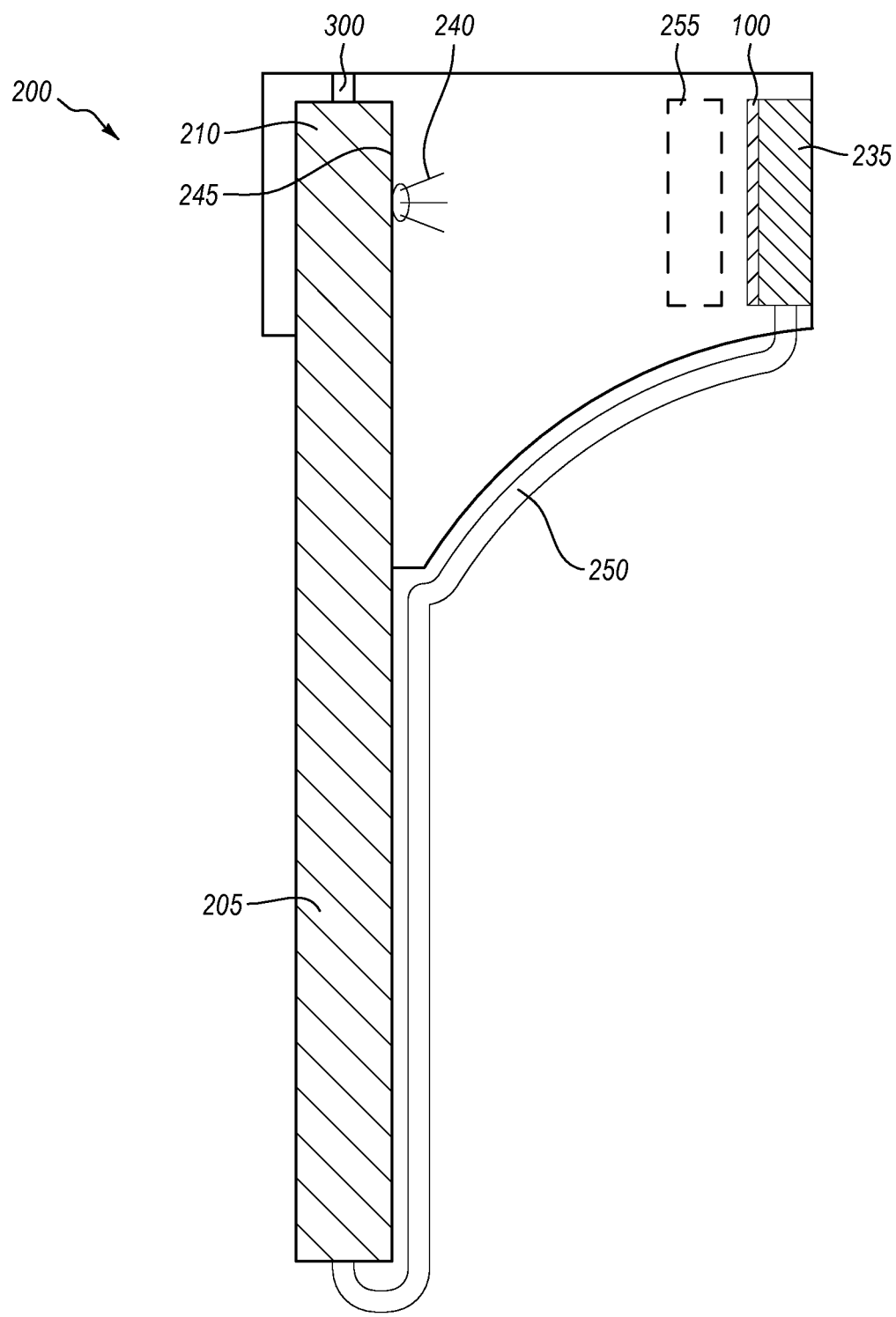
FIG. 2C illustrates a cut-away view of the system of FIG. 2A.

Referring now to FIG. 2C, a cut-away view of the system 200 of FIGS. 2A and 2B is illustrated. The cut-away view illustrates the relationship between the testing device 205 and the testing apparatus 210 and illustrates the components that are housed in the testing apparatus 210 itself. The primary component of the testing apparatus 210 is an image sensor 235 that is electrically connected 250 to the testing device. As will be explained in greater detail below, the image sensor 235 can be used for lensless imaging of a peripheral blood smear 100, which is shown positioned atop the image sensor 235.

The testing apparatus further includes a light source 240 that is configured to provide illumination for imaging the peripheral blood smear 100. In addition, the testing device includes a camera device that is indicated at 245. The camera device can be used, for example, for monitoring alignment of the peripheral blood smear 100 relative to the image sensor and/or for test documentation. In the illustrated embodiment, the light source 240 is a component (e.g., a camera flash or an autofocus illuminator) of the testing device 205. Nevertheless, the light source may also be separate from the testing device 205 and instead be a component included in the testing apparatus 210. The device 205 further includes an indexing device 300 that can be inserted into the testing device 205 to align the testing apparatus relative to the testing device 205. The device 205 further includes optional components indicated at 255, which may include one or more lenses that can focus light on the peripheral blood smear, wavelength filter(s), light guides, light conducting fibers, and the like.

The peripheral blood smear 100 chip can be directly imaged with the image sensor 235 and cells in the smear 100 can be counted can be counted and classified by automatic cell counting software. These steps can be accomplished rapidly (e.g., in less than a minute).

To image cells in the peripheral blood smear 100 with the image sensor 235, the glass slide 110 is placed in the image sensor 235 and illuminated with the light source 240. A complete image of the peripheral blood smear 100 that is placed atop the image sensor can be captured in approximately one second or less. The cells will be seen in shadow mode, with the size and shape of the shadows being characteristic of the size and shape of the individual cells. The image sensor 235 is chosen such that the size of the individual pixels of the image sensor 235 are small enough to image individual cells. For example, red blood cells are about 6-8 μm in size. Therefore it is preferable, that the pixel size of the image sensor 235 be in a range from about 1 μm to about 10 μm or in a range from about 4 μm to about 8 μm. There are many CCD, CMOS, and hybrid sensors available in the market that have sufficient resolution and that can be used to image at least the "zone of morphology" portion of a peripheral blood smear 100.

Suitable, commercially available examples of image sensors that can be adapted for lensless imaging of peripheral blood smears (or microfluidic devices) include, but are not limited to, the MT9M001 1.3-Megapixel, ½-Inch, Color, CMOS image sensor, which has a pixel size of 5.2 μm×5.2 μm, and the MT9V022 ⅓-Inch, Wide VGA CMOS Image Sensor, which has a pixel size of 6 μm×6 μm, both of which are available from Micron Technologies.

The light emitted by the light source 240 may be assumed as planar light source, if the light source 240 is set up far from the peripheral blood smear 100 and the image sensor 235 as it is in FIG. 2C. Additionally, the light may be passed through a light guide to further planarize the illumination, one or more lenses that can focus light on the peripheral blood smear, wavelength filter(s), light guides, light conducting fibers, and the like. These are schematically shown at 255.

Generally, the peripheral blood smear 100 is positioned directly atop the image sensor 235. When the distance between the peripheral blood smear 100 and the image sensor 235 is increased, the ring diameter of the cell shadows increases. This effect is observed until the signal-to-noise ration between the shadow and background light intensity exceeds the detection limit of the image sensor pixels. As such, it is generally true that the best image quality is achieved when the glass slide 110 that includes the peripheral blood smear 100 is positioned directly atop the image sensor 235. However, a thin protective layer may be placed over the image sensor 235 to protect the image sensor surface.

An automatic cell counting software can resolve a threshold signal level, which determines the boundaries between cell membranes and background. The images captured by the image sensor 235 can be analyzed to count cells and characterize a distribution of cells as a function of distance from the channel inlet using the public domain NIH Image program (developed at the U.S. National Institutes of Health and available on the Internet at http://rsb.info.nih.gov/nih-image/). Other cell counting and classifying algorithms can be used as well. For example, Octavia from Diffmaster and DM96 from Cellavision are two commercially available programs that have been developed for automated counting and classification of cells in peripheral blood smears.

Figure 2D:
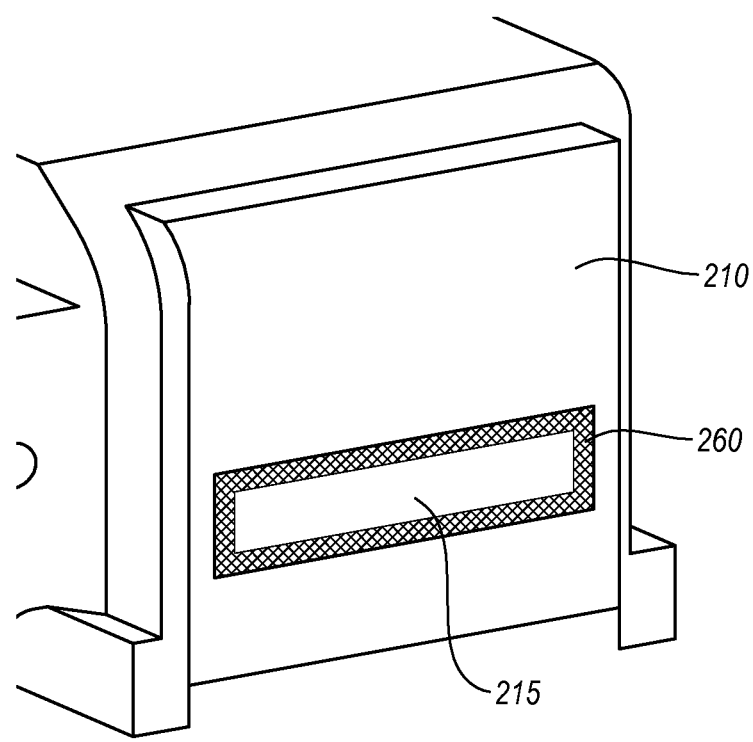
FIG. 2D illustrates a view of a component of the diagnostic test system shown in FIG. 2B, wherein the component includes a light sealing feature.

Referring now to FIG. 2D, the portion of the testing apparatus 210 that includes the port 215 is illustrated greater detail. In the embodiment illustrated in FIG. 2D, the port 215 of the testing apparatus 210 includes a sealing gasket 260 disposed around the port 215 that can seal the port 215 when a glass slide 110 having a peripheral blood smear 100 thereon is inserted into the testing apparatus 210. Because the image sensor 235 is very sensitive, it is important that ambient light does not leak into the testing apparatus 210. For example, if ambient light leaks into the testing apparatus 210, it could skew results. In addition, the port 215 may include a spring-loaded flap (not shown) or similar means that can seal ambient light out of the testing apparatus 210 even when no glass slide 110 is inserted into the port 215.

In an alternative embodiment, a microfluidic device (e.g., a microfluidic flow cytometer) may be used instead of a peripheral blood smear for separation of and counting blood cells. In one embodiment, whole blood may be diluted and transferred into the flow channel of the microfluidic device and counted. By placing the microfluidic device atop the image sensor of the testing device described herein, the flow channel of the microfluidic device and the cells flowing through can be imaged and the cells can be counted. The differential counting systems described herein can be used to count the cells flowing through the flow channel and classify them according the cell type. In another embodiment, a white blood cell count may be performed using a microfluidic device by lysing the red blood cells in whole blood, separating the lysed cells from the white blood cells, and delivering the white blood cells into a flow channel of a microfluidic device. The white blood cells can be counted as described above. In another embodiment, the white blood cells can be separated into individual droplets of phase separated liquid prior to being delivered into the flow channel of the microfluidic device for imaging and counting.

Figure 3:
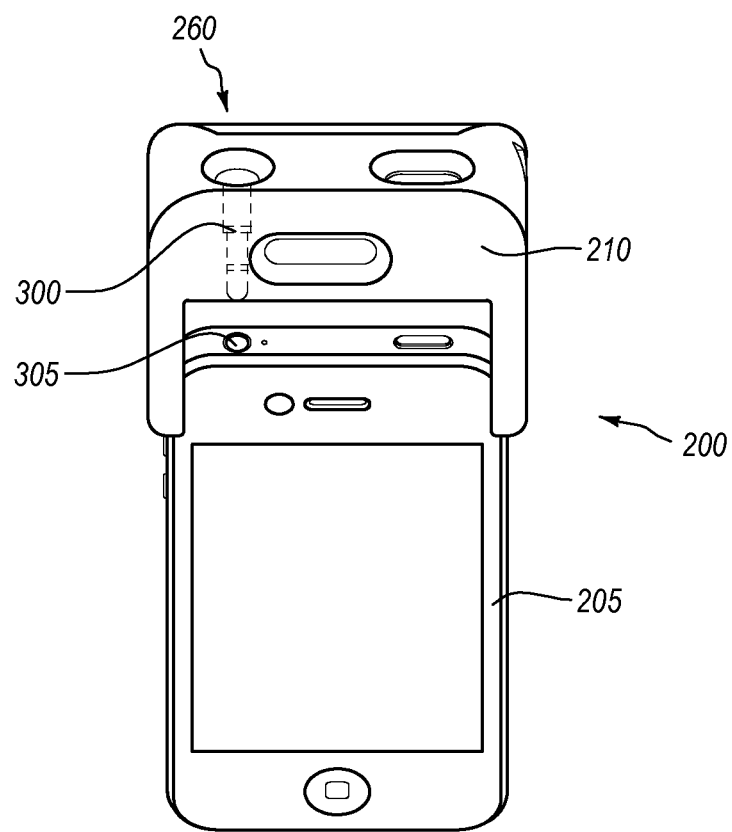
FIG. 3 illustrates a view of a system for performing an automated blood, cell, and/or pathogen count that includes an indexing feature for aligning the testing device with the testing apparatus.

Referring now to FIG. 3, an example of an indexing feature that can reliably align the testing apparatus 210 relative to the testing device 205 is illustrated. In the illustrated embodiment, the indexing feature includes a headphone jack 300 that is integrated into the testing apparatus 210. When the testing device 205 is mated to the testing apparatus 210, the headphone jack 300 is positioned such that it can be inserted into the headphone port 305 of the testing device 205. It will be understood by persons having ordinary skill in the art that headphone jack 300 is but one example of a indexing feature and that additional indexing features can be employed without departing from the spirit of this discussion.

In addition to aligning the testing apparatus 210 relative to the testing device 205, the headphone jack 300 can be used to draw electrical power from the testing device 205 in order to power the image sensor (FIG. 2C, element 235) or another component (e.g., one or more illumination devices) that are positioned in the testing apparatus 210. Likewise, the headphone jack 300 can be used for data transfer between the testing device 205 and components in the testing apparatus 210.

Figure 4:
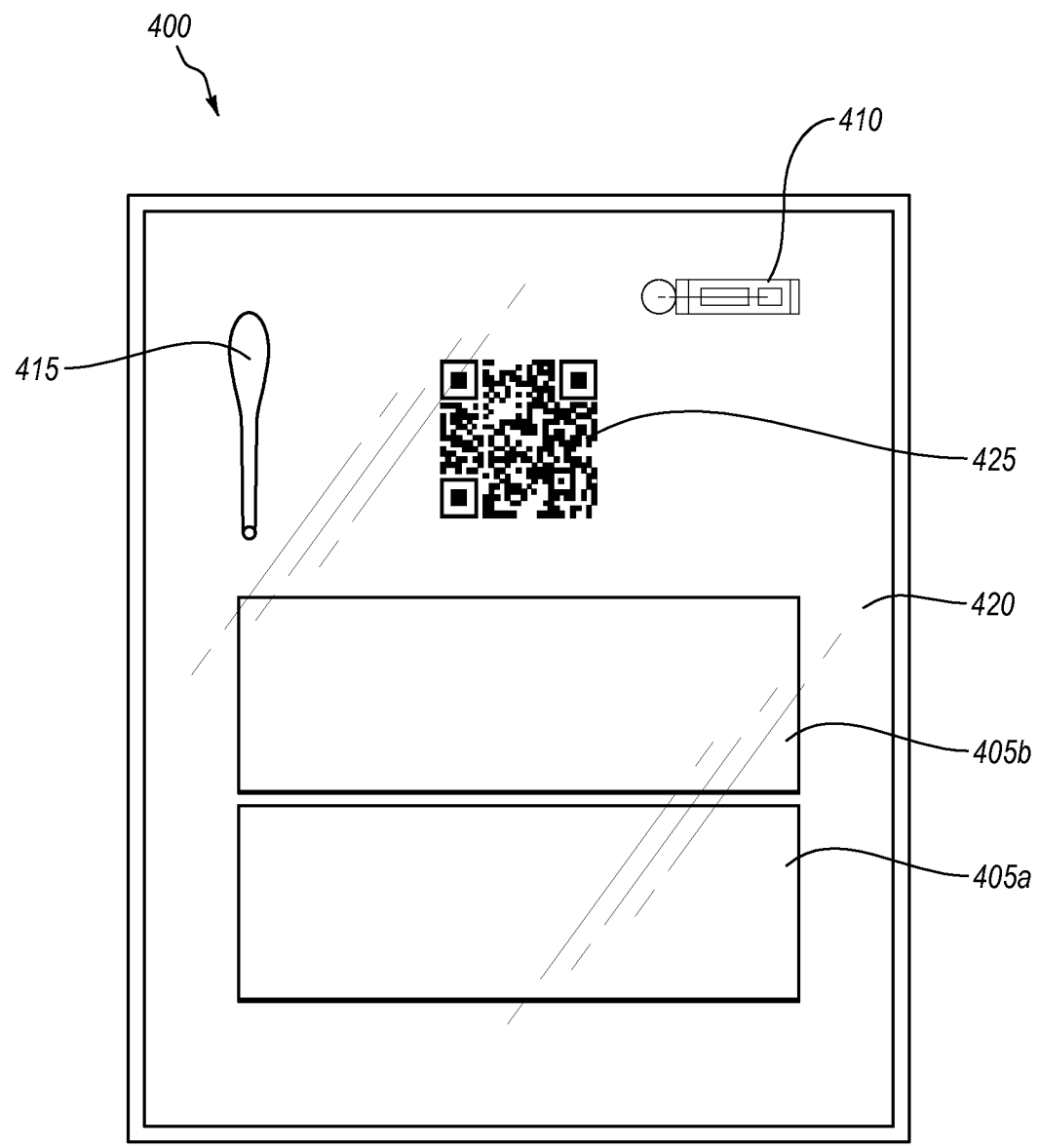
FIG. 4 illustrates a transparent slide suitable for making a peripheral blood smear in a packaging system that includes a tracking feature readable by a testing handheld device.

Referring now to FIG. 4, an embodiment of a packaging system 400 for providing components for preparing and tracking a peripheral blood smear are illustrated. The packaging system 400 includes a sealed package 420 (e.g., a plastic- or paper-based package) that can be used for containing, storing, or transporting, in a clean and preferably sterile environment, the components for preparing a peripheral blood smear. The components in the package 400 may include, but are not limited to, two glass microscope slides 405a and 405b, a disposable lancet 410 or a similar device for pricking a subject's skin, and a pipette 415 for collecting a blood sample. The blood sample may be spotted onto one of the slides (e.g., 405a) and the other slide (e.g., 405b) can be used as a spreader to prepare the peripheral blood smear.

In addition, the packaging system 400 includes a tracking code 425. In the illustrated embodiment, the tracking code 425 is a QR code, which is a two-dimensional bar code. Two-dimensional bar codes, like QR codes, can be used to store far more information that can be stored in a conventional bar code. For example, a QR code can be used to store up ~4300 alphanumeric characters (i.e., 0-9, A-Z, space, $, %, *, +, −, ., /, :, etc.). In one embodiment, the tracking code 425 can be read by the testing device to initiate a test. The tracking code 425 may be used to store information that is relevant to the test in a format that can be read by the device. For example, the tracking code 425 can be used for recording and then transmitting to the test system information about the test to be run, the analysis algorithm to be used, patient information, sample/results tracking, and the like.

II. Methods for Performing an Automated Blood, Cell, and/or Pathogen Count

In one embodiment, a method for performing an automated blood, cell, and/or pathogen count is disclosed. The method includes (1) providing a means for performing a blood, cell, and/or pathogen count, (2) preparing a blood sample for counting using the means, (3) providing a testing device having data collection and data analysis capabilities and the ability to interface with the means for means for performing the blood, cell, and/or pathogen count, and (4) inserting the means for means for performing the blood, cell, and/or pathogen count into a testing apparatus. The testing apparatus includes an image sensor, and a port configured such that the means for means for performing the blood, cell, and/or pathogen count can be inserted into the testing apparatus and positioned in proximity to the image sensor.

The method further includes (5) illuminating the blood sample with at least one wavelength of light configured to allow the image sensor to capture at least one image of the blood sample, and (6) querying an automated counting system stored in a computer readable format and electronically coupled to the testing device, wherein the automated counting system is configured to count individual cells in at least a portion of the blood sample and classify them according to cell type.

Suitable examples of means for performing a blood, cell, and/or pathogen count include, but are not limited to, a glass side or the like configured for preparing a peripheral blood smear or a microfluidic device configured for performing a cell count. In one embodiment, the microfluidic device may include a body that includes a counting chamber configured for performing a cell count and at least one fluid channel in fluid communication with the counting chamber for introducing a sample into the counting chamber, wherein the counting chamber includes a fixative for immobilizing one or more cells present in the sample in the counting chamber.

In one embodiment, the means for performing a blood, cell, and/or pathogen count may include at least one cell-specific antibody that can make it possible to selectively capture and/or image selected cells in the sample prepared thereon. For example, the cells specific antibody can be used to selectively image and count $CD4^+$ T lymphocyte cells or another white blood cell type. In one embodiment, selective imaging of selected cells in the means for performing a blood, cell, and/or pathogen count is facilitated by coupling the cells to be counted to at least one detectable label. Suitable examples of detectable labels include, but are not limited to, colored beads, colloidal gold, colloidal silver, titanium and other microparticles, dyes, fluorescent dyes, europium, quantum dots, enzymes, and combinations thereof. In one embodiment, the detectable label may be coupled to at least one cell-specific antibody.

In one embodiment, the cell-specific antibody can be added to the blood cells prior to preparing the blood sample. In another embodiment, the cell-specific antibody can be added to the blood sample prepared using the means after preparing the sample. In that case, the cell-specific antibody may, for example, be added to the blood cells during a typical staining procedure. In either case, excess or non-specifically bound antibodies can be removed by including a washing step.

In one embodiment, selective imaging of selected cells in the means for performing a blood, cell, and/or pathogen count is facilitated by coupling the at least one cell-specific antibody to at least one detectable label. Suitable examples of detectable labels include, but are not limited to, colored beads, colloidal gold, colloidal silver, dyes, fluorescent dyes, europium, quantum dots, enzymes, titanium and other microparticles and combinations thereof. Such detectable labels can be selectively imaged using, for example, fluorescence techniques.

In one embodiment, the automated counting system queried in the above described method may include one or more computer storage media having stored thereon computer executable instructions that, when executed by one or more processors of the detector device, implement a method for counting and classifying the cells in the blood sample prepared using the means described herein. Results of counting and classifying the cells in the blood sample can be on a screen located on the testing device and/or stored, interpreted, or sent to a database.

In one embodiment, the computer implemented method may further include at least one of: (1) communicating with an electronic medical records system via a wireless communication channel, (2) uploading the image of the prepared blood sample to an electronic database for assessment by a medical technologist, (3) uploading the image of the prepared blood sample to an electronic database for analysis by an automated cell counting system, or (4) querying a decision support algorithm, wherein the decision support algorithm uses the numbers and classes of cells to support a diagnosis of at least one condition in a subject and to suggest a course of treatment.

Embodiments of the present disclosure may comprise or utilize special purpose or general-purpose computing devices that include computer hardware, such as, for example, one or more processors and system memory, as discussed in greater detail below. Embodiments within the scope of the present invention also include physical and other computer-readable and recordable type media for carrying or storing computer-executable instructions and/or data structures. Such computer-readable recordable media can be any available media that can be accessed by a general purpose or special purpose computer system. Computer-readable media that store computer-executable instructions according to the invention are recordable-type storage media or other physical computer storage media (devices) that are distinguished from mere transitory carrier waves.

Computer-readable media that carry computer-executable instructions are transmission media. Thus, by way of example, and not limitation, embodiments of the invention can comprise at least two distinctly different kinds of computer-readable recordable media: computer storage media (devices) and transmission media.

Computer storage media (devices) includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multi-processor systems, microprocessor-based or programmable consumer electronics, network PCs, minicomputers, mainframe computers, tablets, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In particular, one or more embodiments of the invention may be practiced with mobile consumer computing devices. Mobile consumer computing devices or more simply, mobile consumer devices, can be any of a broad range of computing devices designed or optimized for portability and for personal use. Mobile consumer devices can take a variety of forms, ranging from more traditional notebook and netbook computers to an emerging and rapidly growing market of handheld devices, including smart phones (e.g., the APPLE IPHONE, ANDROID phones, WINDOWS phones, SYMBIAN phones), tablet computers (e.g., the APPLE IPAD, ANDROID tablets), gaming devices (e.g., NINTENDO or PLAYSTATION portable gaming devices, the APPLE IPOD), multimedia devices (e.g., the APPLE IPOD), and combinations thereof. Many of these devices can enable rich user-interactivity by including combinations of output, input, and other sensory devices, such as touch- or pressure-sensitive displays (using capacitive or resistive technologies, for example), still and video cameras, Global Positioning System (GPS) receivers, magnetic compasses, gyroscopes, accelerometers, light sensors, proximity sensors, microphones, speakers, etc. These devices can also comprise a variety of communications devices, such as combinations of cellular modems (e.g., Global System for Mobile Communications (GSM), Code division multiple access (CDMA)), Wireless Fidelity (Wi-Fi) radios, Bluetooth radios, Near Field Communication (NFC) devices, etc. Many mobile consumer devices are expandable, such that a user can add new hardware and functionality not present during manufacture of the device. It will be appreciated that as the market for mobile consumer devices expands and develops, the functionality of these devices will also expand to utilize new and improved user-interaction devices and communications devices. The embodiments described herein are expansive and can also utilize any future developments in the field of mobile consumer devices.

III. Microfluidic Devices and Systems Incorporating Such Devices

The embodiments described here relate to point-of-care diagnostic devices and methods for using such devices. In one embodiment, the platform used for such point-of-care diagnostic devices is a smartphone or a similar remote computing device. By leveraging the imaging, computing, and communication components found in a smartphone, the point-of-care diagnostic technology described herein creates a powerful and precise diagnostic instrument that can provide the same quality of clinical information as expensive laboratory equipment found in laboratories, clinics, and doctor's offices.

A smartphone application ("app"), which can be installed on any brand of smartphone, uses one or more of the phone's flash, camera, computation, and data transmission features to collect and quantify diagnostic test information, immunochromatographic, and clinical chemistry assays. The test results can be displayed on the smartphone's screen, sent to a printer, or encrypted and transmitted to a database with date, time, location, and patient information.

The point-of-care diagnostic technology described herein performs in minutes many of the diagnostic tests routinely used in clinical medicine. These tests include, but are not limited to, immunoassays for TSH, PSA, hCG, LH, cortisol, troponin i, clinical chemistry measurement of creatinine and bilirubin, cellular assays (e.g., a complete blood count ("CBC")), identifying infectious bacteria in bodily fluid or another fluid (e.g., drinking water, etc.), amongst others. The point-of-care diagnostic devices described herein cost a fraction of the price of laboratory and desktop instruments, works virtually anywhere that humans inhabit, and can be used by anyone with any model of smartphone or another handheld computing device.

In one embodiment, a microfluidic device for performing a cell count is described. In one embodiment, the microfluidic device includes a body that includes a counting chamber configured for performing a cell count and at least one fluid channel in fluid communication with the counting chamber for introducing a sample into the counting chamber, wherein the counting chamber includes a fixative for immobilizing one or more cells present in the sample in the counting chamber.

In one embodiment, the at least one fluid channel further includes (1) a sample port and a dilution port in fluid communication with a dilution chamber, the dilution chamber being in fluid communication with the counting chamber, (2) a stain port in fluid communication with the counting chamber and configured for introducing at least one cell contrast stain into the counting chamber, (3) at least one wash port in fluid communication with the counting chamber and configured for introducing at least one washing buffer into the counting chamber, a chamber for measuring hemoglobin concentration and (4) a waste chamber in fluid communication with the counting chamber and configured for capturing waste fluid from the counting chamber.

In one embodiment, the at least one fluid channel further includes one or more gate valves or similar microfluidic structures positioned and configured to direct movement of fluid through the least one fluid channel. In one embodiment, the at least one fluid channel may include a sample reservoir configured for measuring a predetermined volume of the sample. In one embodiment, for blood assays (e.g., CBC) in particular, the at least one fluid channel may further include a hemoglobin determination cell in fluid communication with the at least one fluid channel and separate from the counting chamber.

In one embodiment, the at least one fluid channel further includes (1) a first reservoir containing a predetermined amount of a dilution buffer in fluid communication with a dilution chamber, the dilution chamber being in fluid communication with the counting chamber, (2) a second reservoir containing a predetermined amount of a stain in fluid communication with the counting chamber, and (3) at least a third reservoir containing a predetermined amount of a wash buffer in fluid communication with the counting chamber. In one embodiment, the first reservoir, the second reservoir, and the at least third reservoir include blister packs configured to be punctured for successively introducing each of the dilution buffer, the stain, and the wash buffer into the at least one fluid channel.

In one embodiment, the reservoir of dilution buffer may include a volume of liquid selected for diluting a sample (e.g., a blood sample) by a selected dilution factor. For example, for a CBC determination, a blood sample needs to be diluted sufficiently to allow single cells to be discerned while still representing a representative sample. For example, blood needs to be diluted about 1:2000 for counting in a hemocytometer. In order to track the dilution factor applied to the sample in the microfluidic cell described herein, the dilution buffer may include at least one tracer substance (e.g., colored beads or the like) configured for determining the amount of dilution buffer added to the sample. For example, the amount of dilution buffer added to the sample can be determined in situ by counting the number of tracers in the counting chamber.

In yet another embodiment, a system for performing an automated blood, cell, and/or pathogen count is described. The system includes a microfluidic device configured for performing a blood, cell, and/or pathogen count. The microfluidic device includes a counting chamber configured for performing a complete blood, cell, and/or pathogen count and at least one fluid channel in fluid communication with the counting chamber for introducing a blood sample into the counting chamber, wherein the counting chamber includes a fixative for immobilizing blood cells the counting chamber.

The system further includes a testing apparatus communicatively coupled to a testing device (e.g., a handheld computing device), wherein the testing apparatus includes a port configured such that the microfluidic device can be inserted into the testing apparatus, one or more optical elements selected and positioned for, for example, magnifying an image of one or more blood cells in the counting chamber onto an image sensor, and at least one conduit allowing data transfer back and forth between the image sensor and the handheld device. Suitable examples of optical elements may include, but are not limited to, wavelength filters, diffraction gratings, windows, interferometers, mirrors, and the like. The testing apparatus further includes a light source capable of transmitting at least one wavelength of light configured to allow the image sensor to capture at least one image of at least a portion of the counting chamber of the microfluidic device, wherein the image has a resolution sufficient for discerning individual cells in the image taken of the at least a portion of the counting chamber of the microfluidic device.

When at least one image of cells in the microfluidic device is captured, it may be transmitted to the testing device for image analysis. As such, the system further includes an automated counting system stored in a computer readable format and electronically coupled to the handheld device, wherein the automated counting system is configured to count individual cells in the image taken of at least a portion of the counting chamber of the microfluidic device and classify them according to cell type.

In one embodiment, the system described herein may be configured for performing a complete blood count, including at least one of performing a red blood cell count, a platelet count, a white blood cell count, determining a hematocrit, or determining a hemoglobin concentration. While performing a complete blood count is cited as a specific example of the use of the system, one will appreciate that the system and the microfluidic device can be adapted for performing a number of different assays. Suitable examples of additional assays that the system and the microfluidic device can be adapted to include, but are not limited to, a white blood cell count, a $CD4^+$ T lymphocyte test, identifying abnormal blood cells, identifying infectious disease pathogens within blood cells, identifying different classes of lymphocytes, using other body fluids (e.g. cerebrospinal fluid, urine, sputum, joint fluid, mucus) for cellular analysis, using tissue aspirates suspended in a liquid for cellular analysis, and combinations thereof.

In addition, the stain and/or the counting chamber may include at least one cell-specific antibody selected from the group consisting of a CD4 antibody, lymphocyte typing antibodies, antibodies for detecting bacterial, viral, or parasitic pathogens, antibodies for detecting leukemic cells, antibodies for detecting erythrocyte precursors, antibodies for detecting platelets, antibodies for detecting circulating tumor cells, antibodies for determining host response to pathogens by determining whether endogenous antibodies are bound to pathogens and combinations thereof.

In addition, at least one cell-specific antibody may be combined with a sample prior to adding the sample to the microfluidic device. Examples of cell-specific antibodies include, but are not limited to, CD4 antibody, lymphocyte typing antibodies, antibodies for detecting bacterial, viral, or parasitic pathogens, antibodies for detecting leukemic cells, antibodies for detecting erythrocyte precursors, antibodies for detecting platelets, antibodies for detecting circulating tumor cells, and combinations thereof.

In one embodiment, the at least one cell-specific antibody is coupled to at least one detectable label selected from the group consisting of colored beads, colloidal gold, colloidal silver, dyes, fluorescent dyes, quantum dots, and combinations thereof.

As described above, the microfluidic device may include a number of fluid reservoirs (e.g., blister packs) configured for diluting the sample, staining cells in the sample, and washing away excess stain, unadhered cells, etc. In one embodiment, the testing apparatus may include one or more pressure applying members (e.g., rollers) for successively introducing each of the dilution buffer, the stain, and the wash buffer from the blister packs into the at least one fluid channel. In one embodiment, such pressure applying members may be positioned in or around the microfluidic device insertion port of the testing apparatus.

Figure 5:
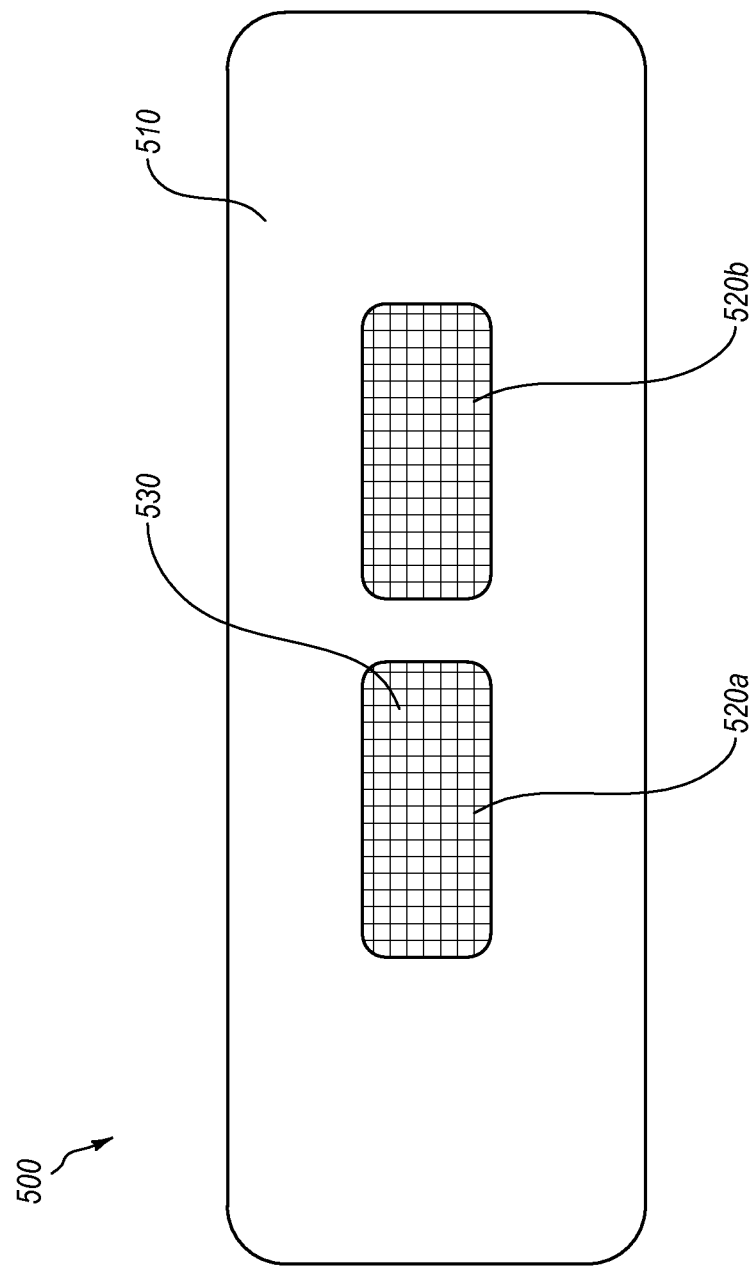
FIG. 5 illustrates a prior art hemocytometer.

Referring now to FIG. 5, a prior art hemocytometer 500 is illustrated. The hemocytometer is a device originally designed for the counting of blood cells. However, it is now also used to count other types of cells as well as other microscopic particles. The hemocytometer 500 includes a body 510 and at least one counting chamber—the embodiment illustrated herein includes two counting chambers 520a and 520b.

The body 510 is typically glass or a similar transparent material. The counting chambers 520a and 520b each include a hemocytometer grid 530 that facilitates the counting of cells.

Hemocytometers are often used to count blood corpuscles, organelles within cells, blood cells in cerebrospinal fluid after performing a lumbar puncture, or other cell types in suspension. Anchorage-dependent cells can also be counted if subjected to trypsinization prior to counting. Using a special hemocytometer with a depth of 0.02 mm smaller particles such as sperm, yeast or bacteria can be counted.

Figure 6:
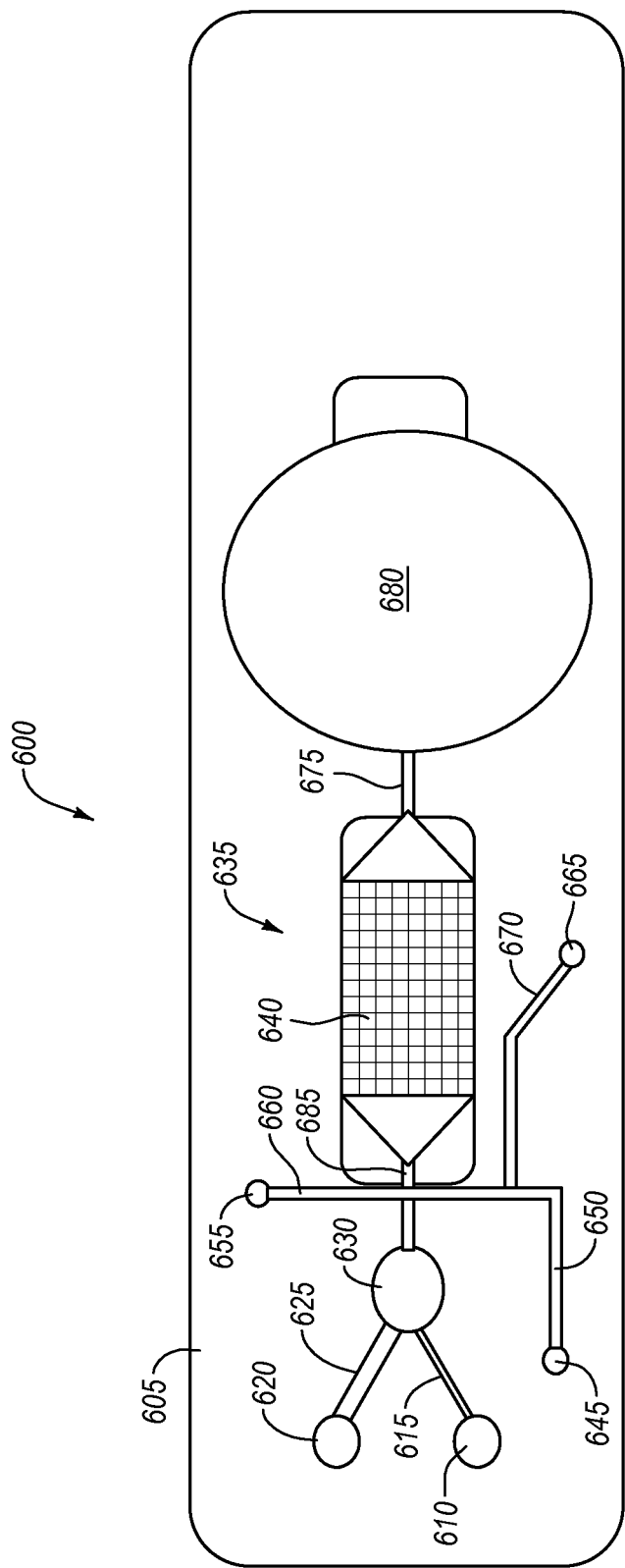
FIG. 6 illustrates a microfluidic device according to one embodiment of the present invention.

Referring now to FIG. 6, one embodiment of a microfluidic device 600 is illustrated. The microfluidic device 600 includes a body 605 that includes a series of fluid ports, fluid channels, and chambers. In one embodiment, the series of fluid ports, fluid channels, and chambers can be integrally formed in the body 605. In another embodiment, the series of fluid ports, fluid channels, and chambers can form in one or more layers (e.g., tape layers) that are overlaid onto the body 605. Suitable examples of materials that can be used to form the body 605 include glass and plastics. For example, the body and the series of fluid ports, fluid channels, and chambers can be integrally formed in a plastic body by injection molding.

In one embodiment, the series of fluid ports, fluid channels, and chambers includes a sample port 610, a dilution port 620, and a dilution chamber 630 that is in fluid communication with the sample port 610 and the dilution port 620. The series of fluid ports, fluid channels, and chambers further includes a counting chamber 635, which includes a counting grid 640, a stain port 645, a first wash port 655, a second wash port 665, and a waste chamber 680 for collecting excess fluids. The ports and chambers are interconnected by a series of fluid channels 615, 625, 650, 660, 670, 675, and 685. In one embodiment, the counting chamber 635 includes a fixative layer for affixing cells in the counting chamber. Suitable examples of fixatives include, but are not limited to, albumin, high molecular weight Poly-Lysine solution (M.W. ~70,000), and aminopropyltriethoxysilane.

In one embodiment, the microfluidic device may be used as follows for preparing a blood smear for performing a blood, cell, and/or pathogen count:

Introduce blood and diluent (e.g., PBS) into the dilution chamber.

Diluted blood is then sent through microfluidic channel network to counting chamber where cells bind to the surface.

1st Wash step (Wash Port 1): Use PBS to remove excess cell debris leaving a monolayer of cells in the chamber.

Staining step (Stain Port): introduce staining fluid (e.g., Wright's stain) into the counting chamber to stain the monolayer of cells 2nd Wash step (Wash Port 2): Use PBS to wash cells and remove stain from chamber Image the counting chamber for counting.

Figure 7:
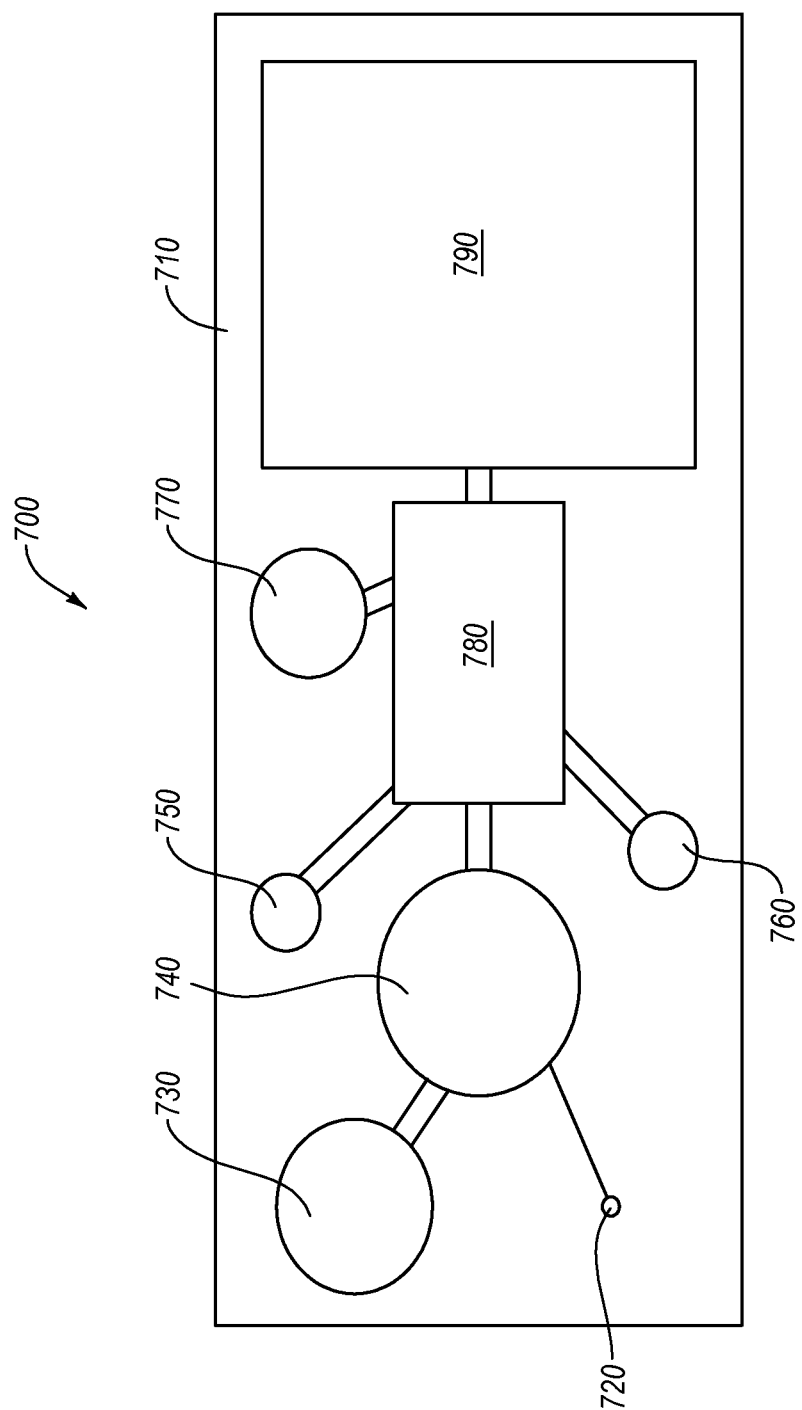
FIG. 7 illustrates a microfluidic device according to one embodiment of the present invention.

Referring now to FIG. 7, a microfluidic device 700 similar to what is shown in FIG. 6 is illustrated. Microfluidic device 700 includes a body 710, a blood port 720, a dilution chamber 740, a counting chamber 780, and a waste chamber 790. The microfluidic device 700 is different from microfluidic device 600 in that the dilution, wash, and stain ports are replaced with a series of reservoirs. This series of reservoirs include a dilution buffer reservoir 730, a stain reservoir 750, a first wash reservoir 760, and an optional second wash reservoir 770. These reservoirs, which may, for example, be provided as blister packs that can be punctured to deliver their fluid, can be used to introduce dilution buffer, stain, and wash buffer as in the steps described above. As such, the device 700 illustrated in FIG. 7 is self-contained. Thus, there is no reason for a user to carry separate containers of buffer and stain. Instead, the only thing that need be added to the microfluidic device 700 is blood or another fluid of interest (via the blood port). The sample can be diluted, washed, and stained by successively introducing the buffers and stains from the reservoirs.

Figure 8:
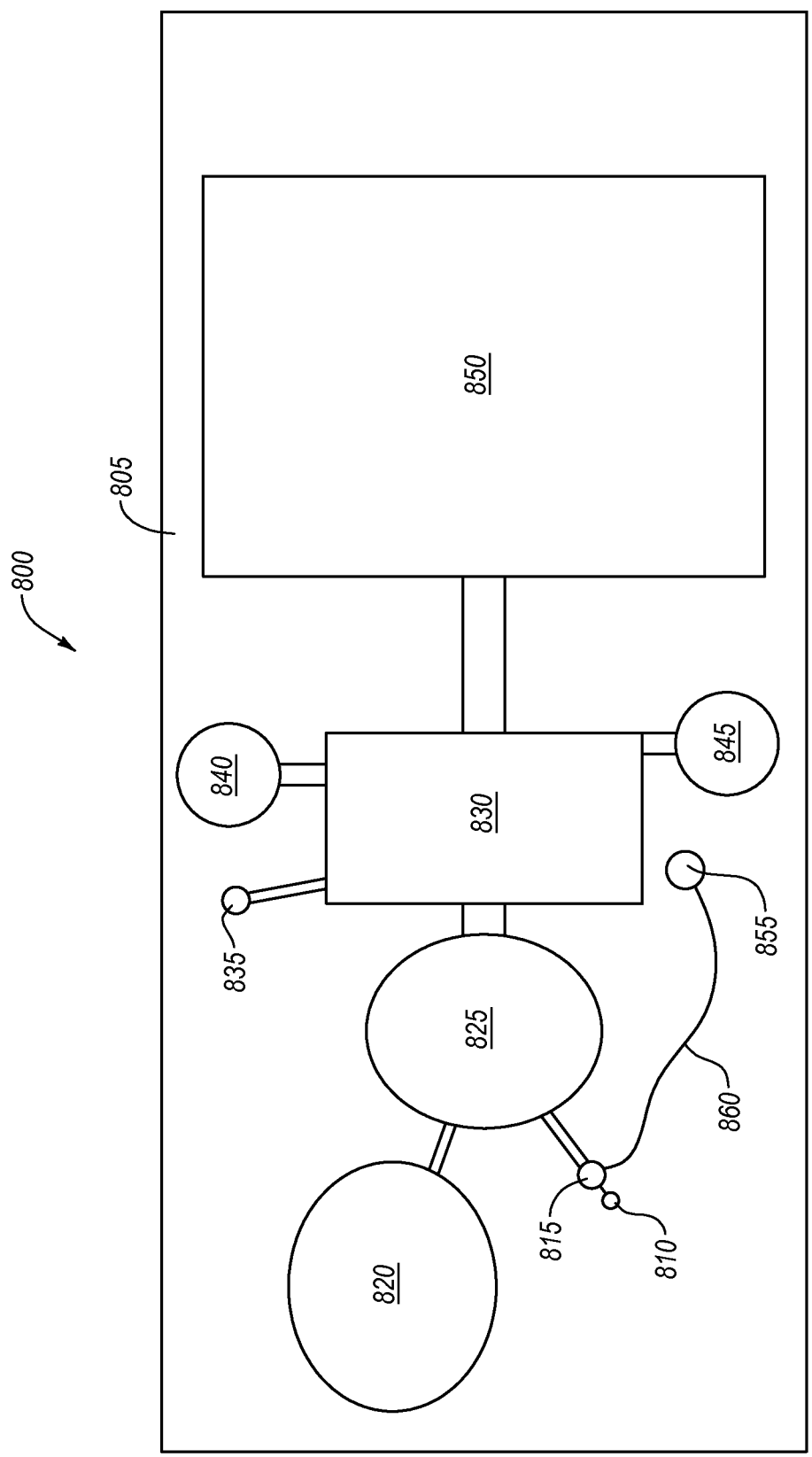
FIG. 8 illustrates a microfluidic device according to one embodiment of the present invention.

Referring now to FIG. 8 a microfluidic device 800 similar to what is shown in FIGS. 6 and 7 is illustrated. Microfluidic device 800 is different from microfluidic device 700 primarily in that the sample port 810 includes a chamber 815 for measuring a selected sample volume (e.g., a volume that can be effectively used for obtaining a representative sample and that can be sufficiently diluted by the volume of buffer in the buffer reservoir 820). In addition, in an application specific for a complete blood count, the microfluidic device 800 includes a separate chamber 855 that can be used for determining a hemoglobin concentration.

Figure 9:
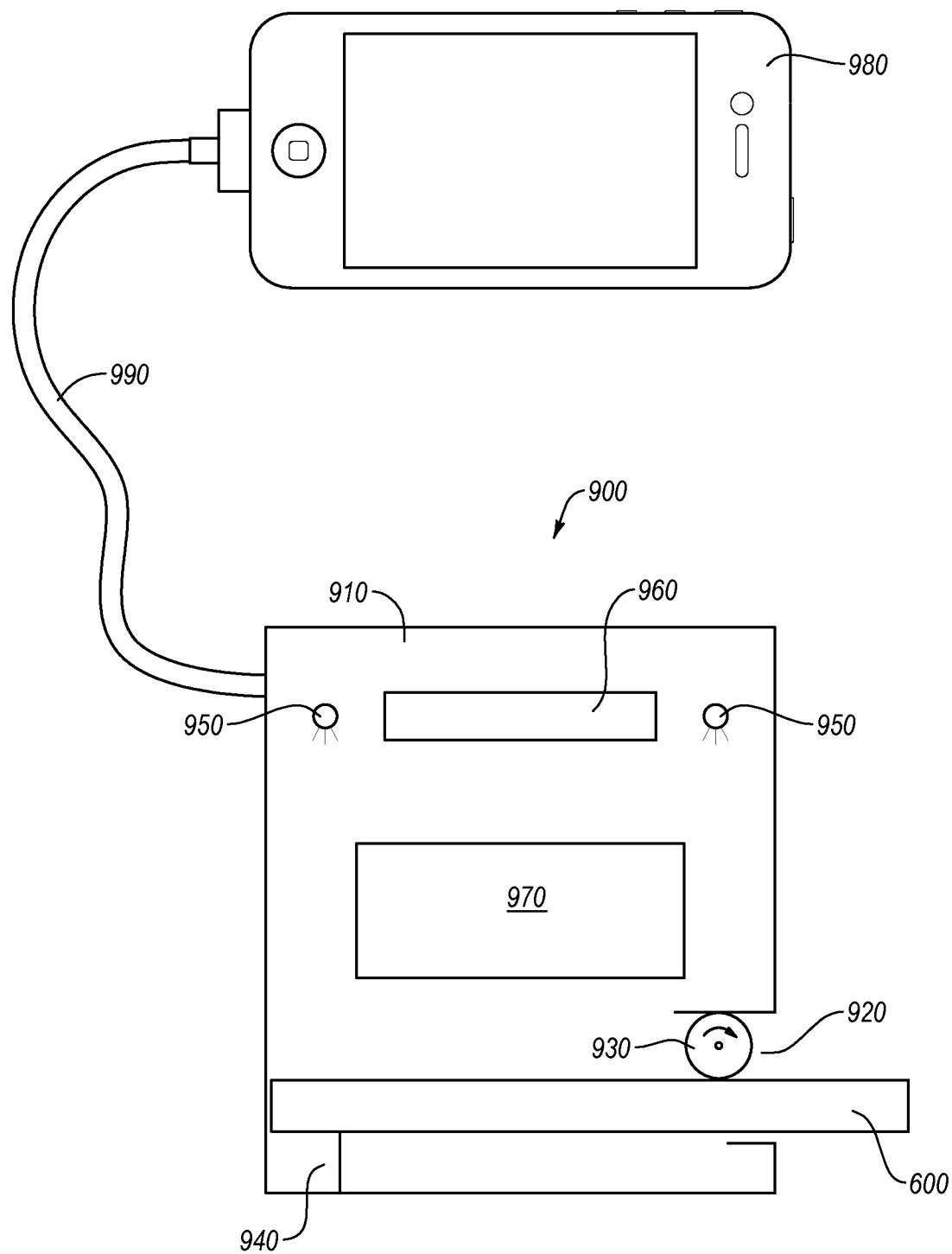
FIG. 9 illustrates a testing apparatus according to one embodiment of the present invention.

Referring now to FIG. 9, a testing apparatus 900 that can be communicatively coupled 990 to a smartphone 980 (or a similar device) is illustrated. The testing apparatus 900 includes a housing 910 that can be configured to receive a microfluidic device (e.g., device 600) through port 920. In the illustrated embodiment, the housing 910 includes an image sensor 960, at least one light source 950 (e.g., a white light source or lights selected to emit selected wavelengths) and at least one optical element 970 that is selected and configured to project a magnified image of at least a portion of the microfluidic device 600 onto the image sensor 960. The magnification factor of the optical element 970 will depend on the assay being performed. For example, CBCs are typically counted under ~600× magnification. However, because of the resolution powers of image sensor chips (e.g., CMOS or CDC chips) it may be possible, if the pixel size of the chip is sufficiently small and the signal-to-noise ratio is sufficient, to collect an image of a counting chamber at, for example, ~60× and then magnify the image for counting by an automated counting program. One will appreciate that the relative arrangement of the optical element(s) 970, the image sensor 960, the lights 950, and the microfluidic device 600 can be altered depending on various illumination and detection techniques (e.g., bright field, oblique illumination, dark field, phase contrast, etc.).

In one embodiment, the housing 910 may also include one or more pressure applying members 930 (e.g., rollers) that are positioned and configured to accomplish the dilution buffer dispensing, mixing, staining, and washing steps for using a microfluidic device that includes self-contained fluids (e.g., device 700 or 800). In such an embodiment, all that a user would have to do to, for example, perform a CBC would be to add the blood sample to the microfluidic device and insert it into the housing 910. In such an embodiment, the one or more pressure applying members 930 would be positioned for successively introducing each of the dilution buffer, the stain, and the wash buffer from the reservoirs into the appropriate portions of the fluid channel.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A point-of-care system for performing an automated cell count, comprising:

means for performing a blood, cell, and/or pathogen count;

a testing device for data collection and data analysis the testing device comprising a handheld computing device that includes one or more processors and one or more computer readable media having stored thereon computer-executable instructions that are executable by the one or more processors to reprogram the handheld computing device with an automated counting algorithm that uses the handheld computing device to count individual cells in at least a portion of an image and classify them according to cell type;

a sample holder coupled to the testing device, the sample holder comprising housing and a port configured to receive the means for performing a blood, cell, and/or pathogen count and position it in proximity to an image sensor of the testing device and a light source, wherein the sample holder is configured to control for focal length from the image sensor to the means for performing a blood, cell, and/or pathogen count and to control for illumination from the light source to the means for performing a blood, cell, and/or pathogen count;

the light source being configured for transmitting at least one wavelength of light configured to allow the image sensor to capture at least one image of the means for performing a blood, cell, and/or pathogen count; and, the image sensor being configured to collect an image of sufficient resolution for discerning individual cells in the image taken of the means for performing the blood, cell, and/or pathogen count, wherein the handheld computing device is selected from the group consisting of a handheld digital camera, a camera phone, a smartphone, or a tablet computer.

2. The system of claim 1, wherein the pixel size of the image sensor is in a range from about 1 μm to about 10 μm.

3. The system of claim 1, wherein the pixel size of the image sensor is in a range from about 4 μm to about 8 μm.

4. The system of claim 1, wherein the sample holder includes at least one indexing feature configured to align the sample holder with the testing device.

5. The system of claim 1, wherein the housing includes one or more seals to create a light-tight environment between the testing device and the housing and between the housing and the means for performing a blood, cell, and/or pathogen count.

6. The testing system of claim 1, wherein the testing device is capable of communicating with a cellular telephone network.

7. The system of claim 1, wherein the light source is at least one of a camera flash, an autofocus illuminator, ambient light, sunlight, an LED light, an incandescent lamp, or a gas-discharge lamp.

8. The system of claim 1, wherein at least one of a lens, a wavelength filter, a light conducting fiber, or a light guide is interposed between the light source and the image sensor.

9. The system of claim 1, wherein the system is configured for performing a test selected from the group consisting of a complete blood count, a white blood cell count, a $CD4^+$ T lymphocyte test, identifying abnormal blood cells, identifying infectious disease pathogens within blood cells, identifying different classes of lymphocytes, using other body fluids (e.g. cerebrospinal fluid, urine, sputum, joint fluid, mucus) for cellular analysis, using tissue aspirates suspended in a liquid for cellular analysis, and combinations thereof.

10. The system of claim 1, wherein the means for performing a blood, cell, and/or pathogen count is one of a peripheral blood smear or a microfluidic device configured for performing a cell count.

11. The system of claim 10, wherein the microfluidic device includes a body that includes a counting chamber configured for performing a cell count and at least one fluid channel in fluid communication with the counting chamber for introducing a sample into the counting chamber, wherein the counting chamber includes a fixative for immobilizing one or more cells present in the sample in the counting chamber.

12. The system of claim 11, wherein the at least one fluid channel further comprises (1) a sample port and a dilution port in fluid communication with a dilution chamber, the dilution chamber being in fluid communication with the counting chamber, (2) a stain port in fluid communication with the counting chamber and configured for introducing at least one cell contrast stain into the counting chamber, (3) at least one wash port in fluid communication with the counting chamber and configured for introducing at least one washing buffer into the counting chamber, and (4) a waste chamber in fluid communication with the counting chamber and configured for capturing waste fluid from the counting chamber.

13. The system of claim 11, wherein the at least one fluid channel further includes (1) a first reservoir containing a predetermined amount of a dilution buffer in fluid communication with a dilution chamber, the dilution chamber being in fluid communication with the counting chamber, (2) a second reservoir containing a predetermined amount of a stain in fluid communication with the counting chamber, and (3) at least a third reservoir containing a predetermined amount of a wash buffer in fluid communication with the counting chamber.

14. The system of claim 13, wherein one or more of the first reservoir, the second reservoir, and the at least third reservoir include blister packs configured to be punctured for successively introducing each of the dilution buffer, the stain, and the wash buffer into the at least one fluid channel.

15. The system of claim 14, wherein the dilution buffer includes at least one tracer substance configured for determining the amount of dilution buffer added to the sample.

16. The system of claim 11, wherein the counting chamber includes a multitude of intersecting grid lines defining a multitude of counting zones.

17. The system of claim 11, wherein the at least one fluid channel further comprises at least one of
one or more gate valves positioned and configured to direct movement of fluid through the least one fluid channel;
a fixative for fixing cells in the counting chamber, or
a means for drying the cells.

18. The system of claim 11, wherein the at least one fluid channel further comprises a sample reservoir configured for measuring a predetermined volume of the sample.

19. The system of claim 11, wherein the at least one fluid channel further comprises a hemoglobin determination cell in fluid communication with the at least one fluid channel and separate from the counting chamber.

20. A system for performing an automated blood, cell, and/or pathogen count, comprising:
a microfluidic device configured for performing a blood, cell, and/or pathogen count, wherein the microfluidic device includes a counting chamber configured for performing a complete blood, cell, and/or pathogen count and at least one fluid channel in fluid communication with the counting chamber for introducing a cell sample into the counting chamber, wherein the counting chamber includes a fixative for immobilizing cells the counting chamber;
the at least one fluid channel of the microfluidic device further comprising (1) a sample port and a dilution port in fluid communication with a dilution chamber, the dilution chamber being in fluid communication with the counting chamber, (2) a stain port in fluid communication with the counting chamber and configured for introducing at least one cell contrast stain into the counting chamber, (3) at least one wash port in fluid communication with the counting chamber and configured for introducing at least one washing buffer into the counting chamber, (4) a waste chamber in fluid communication with the counting chamber and configured for capturing waste fluid from the counting chamber, and at least one of the sample port, the stain port, or the wash port including a reservoir containing a predetermined amount of a dilution buffer, stain, or wash buffer, respectively;
a sample holder communicatively coupled to a computing device, wherein the sample holder includes a port configured such that the microfluidic device can be inserted into the sample holder, one or more optical elements selected and positioned for magnifying an image of one or more blood cells in the counting chamber onto an image sensor, and at least one conduit allowing data transfer back and forth between the image sensor and the computing device;
a light source capable of transmitting at least one wavelength of light configured to allow the image sensor to capture at least one image of at least a portion of the counting chamber of the microfluidic device, wherein the image sensor has a pixel size sufficient for discerning individual cells in the image taken of the at least a portion of the counting chamber of the microfluidic device; and
an automated counting system stored in a computer readable format and electronically coupled to the computing device, wherein the automated counting system is configured to count individual cells in the image taken of the at least a portion of the counting chamber of the microfluidic device and classify them according to cell type.

* * * * *